(12) United States Patent
Döbert et al.

(10) Patent No.: US 6,441,254 B1
(45) Date of Patent: Aug. 27, 2002

(54) PROCESS FOR PREPARING TRIMETHYLOL COMPOUNDS AND FORMIC ACID

(75) Inventors: Frank Döbert, Köln; Paul Wagner, Düsseldorf; Alexander Klausener, Pulheim; Wolfgang Eymann, Köln; Rolf Feller, Korschenbroich, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/017,816

(22) Filed: Dec. 13, 2001

(30) Foreign Application Priority Data

Dec. 20, 2000 (DE) .......................................... 100 63 937

(51) Int. Cl.⁷ .......................... C07C 31/18; C07C 27/26; C07C 69/00
(52) U.S. Cl. ......................... 568/853; 568/854; 560/129
(58) Field of Search ................................ 568/853, 854; 560/129

(56) References Cited

U.S. PATENT DOCUMENTS

| 4,247,485 A | 1/1981 | Immel et al. ................ 568/464 |
| 4,594,461 A | 6/1986 | Merger et al. ............... 568/853 |
| 4,855,496 A | 8/1989 | Anderson et al. ........... 562/609 |
| 5,149,861 A | 9/1992 | Merger et al. ............... 560/234 |
| 6,018,074 A | 1/2000 | Kratz et al. ................. 560/234 |
| 6,034,284 A | 3/2000 | Doi et al. .................... 568/853 |
| 6,034,285 A | 3/2000 | Doi et al. .................... 568/853 |
| 6,187,974 B1 | 2/2001 | Kratz et al. ................. 568/853 |

FOREIGN PATENT DOCUMENTS

| DE | 1952738 | 7/1970 |
| GB | 1535826 | 12/1978 |

*Primary Examiner*—Samuel Barts
*Assistant Examiner*—Elvis O. Price
(74) *Attorney, Agent, or Firm*—Joseph C. Gil; Richard E. L. Henderson

(57) ABSTRACT

The present invention relates to a process for preparing trimethylol compounds and formic acid by reaction of formaldehyde and aldehydes in the presence of a nitrogen base and distillation of the resulting reaction mixture in the presence of an auxiliary.

12 Claims, 1 Drawing Sheet

PROCESS FOR PREPARING TRIMETHYLOL COMPOUNDS AND FORMIC ACID

BACKGROUND OF THE INVENTION

The present invention relates to a process for preparing trimethylol compounds and formic acid by reaction of formaldehyde and aldehydes in the presence of a nitrogen base followed by distillation of the resulting reaction mixture in the presence of an auxiliary.

Trimethylol compounds are widely used in the plastics sector for producing surface coatings, urethanes, and polyesters. Important trimethylol compounds are, for example, trimethylolethane and trimethylolbutane, but especially trimethylolpropane.

The industrial preparation of trimethylolpropane (TMP) starts out from n-butyraldehyde and formaldehyde that are reacted in a two-stage reaction process. In a first reaction step, 2,2-dimethylolbutanal is formed first in a base-catalyzed aldol condensation via the intermediate 2-methylolbutanal. In a subsequent cross Cannizzaro reaction, trimethylol-propane together with formate salts are formed in the presence of stoichiometric amounts of a base.

As base, use is usually made of inorganic compounds such as sodium hydroxide or calcium hydroxide. If calcium hydroxide is used as base in the process, the calcium formate obtained as coproduct can, for example, be used further for producing various animal fodder products and additives for animal fodder products. However, the sodium formate formed when sodium hydroxide is used is less desirable. In any case, the formation of an inorganic formate salt as coproduct is associated with disadvantages even when it can be utilized: first, the separation of the salt from TMP is complicated and incurs additional costs, while, second, the salt has to be worked up and purified if it is to be utilized in a beneficial fashion.

In an alternative process variant, the reaction of n-butyraldehyde with formaldehyde is carried out in the presence of a tertiary amine, usually a trialkylamine. However, the excesses of formaldehyde and trialkylamine used result in stoichiometric amounts of trialkylammonium formate being formed in addition to TMP. To improve the economics of such a process, it is necessary to recover the amine used from trialkyl-ammonium formate and preferably pass the formate to a purposeful use.

DE 25 07 461 A describes a process for preparing 2,2-dimethylol-alkanals that are converted into the corresponding trimethylol compound in a subsequent hydrogenation. Thus, for example, TMP is prepared by reaction of n-butyraldehyde with formaldehyde in the presence of catalytic amounts of tertiary amines and subsequent hydrogenation of the reaction product. A disadvantage of this process is that only unsatisfactory yields of trimethylolpropane are achieved.

DE 1 952 738 A describes a process for preparing TMP by reaction of n-butyraldehyde with formaldehyde in the presence of tertiary amines. The formate salts formed in the process are separated from TMP by distillation. It is proposed that the trialkylammonium formates thus formed be reacted with an aqueous calcium hydroxide solution to give calcium formate and liberate the amine, which is returned to the reaction circuit. A disadvantage of this process is that, once again, it results in formation of an organic formate salt that, if it is to be utilized further, has to be separated off and purified in a further reaction step. In addition, calcium hydroxide has to be used as additional starting material in order to convert the formate into a usable product.

In EP 142 090 A, TMP is prepared by reacting one mol of n-butyr-aldehyde with from 2.2 to 4.5 mol of formaldehyde and from 0.6 to 3 mol of trialkylamine and catalytically hydrogenating the resulting 2,2-dimethylol-butanal. A disadvantage is that the high amine concentrations in the aldol reaction result in formation of considerable amounts of trialkylammonium formates that have to be separated off by distillation prior to the hydrogenation. Liberation of trialkylamine from the formates formed and recirculation of the base to the process is not described.

In the method of reducing the amount of formate formed described in DE 28 13 201 A, formaldehyde is used in excess but the amine is used only as catalyst for the aldol reaction to form 2,2-dimethylolbutanal. The aldehyde formed is subsequently catalytically hydrogenated. The process is not very suitable for industrial use since the excess of formaldehyde has to be separated off prior to the hydrogenation because of possible poisoning of the hydrogenation catalyst.

EP 289 921 A describes a process for preparing trimethylolalkanes which is similar to that described in EP 142 090 A and in which 1 mol of aldehyde is reacted with from 2.2 to 4.5 mol of formaldehyde in aqueous solution in the presence of from 0.6 to 3 mol of trialkylamine and the product is subsequently hydrogenated. To work up the trialkylammonium formate obtained, two process variants are reported. In variant (a), the crude hydrogenation mixture is heated to 100–200° C. and water and excess trialkylamine are separated off by distillation. The trialkyl-ammonium formate remaining in the bottoms reacts with the alcohol present to give trimethylolalkane formate, thus liberating the amine used. The trimethylolalkane formate is subsequently transesterified with methanol to give methyl formate and trimethylolalkane. In process variant (b), the hydrogenation product is first substantially dewatered and the trialkylammonium formate remaining in the bottoms is subsequently esterified directly with methanol to form methyl formate. A disadvantage of both variants is that a loss of formaldehyde due to catalytic hydrogenation has to be accepted in order to achieve economical yields.

In DE 195 42 036 A, the recirculation of the tertiary amine used as base is carried out via esterification of the trialkylammonium formate formed with polymethylolalkane. A disadvantage of this method is that the ester formed has to be transesterified with a further, lower-boiling alcohol in a further step in order to liberate the polymethylolalkane.

WO 98/28253 A describes a process for preparing TMP without producing a coproduct. Here, n-butyraldehyde is reacted with from 2 to 8 times its molar amount of formaldehyde in a first reaction step in the presence of a tertiary amine as catalyst. The reaction mixture obtained is fractionally distilled in a second stage, where the distillate stream consisting predominantly of unreacted or partially reacted starting materials is returned to the first stage and the bottoms comprising predominantly 2,2-dimethylolalkanal are separated off or the reaction mixture from the first stage is separated by phase separation into an aqueous phase and an organic phase and the organic phase is returned to the first stage. In a third after-reaction stage, the bottoms fraction that has been separated off in the second stage or the aqueous phase obtained by phase separation in the second stage is subjected to a catalytic and/or thermal treatment in which the incompletely reacted compounds are converted into 2,2-dimethyolalkanal and starting materials that are returned to the first stage. Subsequently, 2,2-dimethylolalkanal is hydrogenated in a known manner to produce the corresponding trimethylol compound. However, this process has the disadvantage that the mono-methylolalkanal formed has to be eliminated from the reaction mixture by complicated measures since otherwise relatively large amounts of by-products are formed in the catalytic hydrogenation.

A further process for recovering the amines used is disclosed in DE 198 48 568 A and DE 198 48 569 A. After reaction of the aldehyde with aqueous formaldehyde in the presence of a tertiary amine, the reaction mixture is first freed of free amine and water by distillation. The trialkylammonium formate remaining in the bottoms is concentrated by distillation at a pH of 5 until trimethylolalkane formate and free amine are formed, with the latter being separated off as distillate. The trimethylol-alkane formate is decomposed catalytically under pressure at temperatures of about 280° C. into trimethylolalkane, hydrogen, carbon dioxide, water, and carbon monoxide. A disadvantage of this process is that at least 1 mol equivalent of formaldehyde per mole of alkanal is not utilized economically.

It is therefore an object of the invention to provide a process for preparing trimethylol compounds in the presence of tertiary amines as base that allows the formate salts obtained to be converted into a usable form with recirculation of the amine used.

SUMMARY OF THE INVENTION

We have now surprisingly found a process for preparing trimethylol compounds and formic acid comprising (a) reacting formaldehyde and an aldehyde in the presence of a nitrogen base to form a product mixture containing the trimethylol compound and a formate salt of the nitrogen base, (b) removing the trimethylol compound from the product mixture after the reaction, and (c) cleaving the formate salt into the free nitrogen base and formic acid by distillation in the presence of an auxiliary.

DETAILED DESCRIPTION OF THE INVENTION

Figure 1:
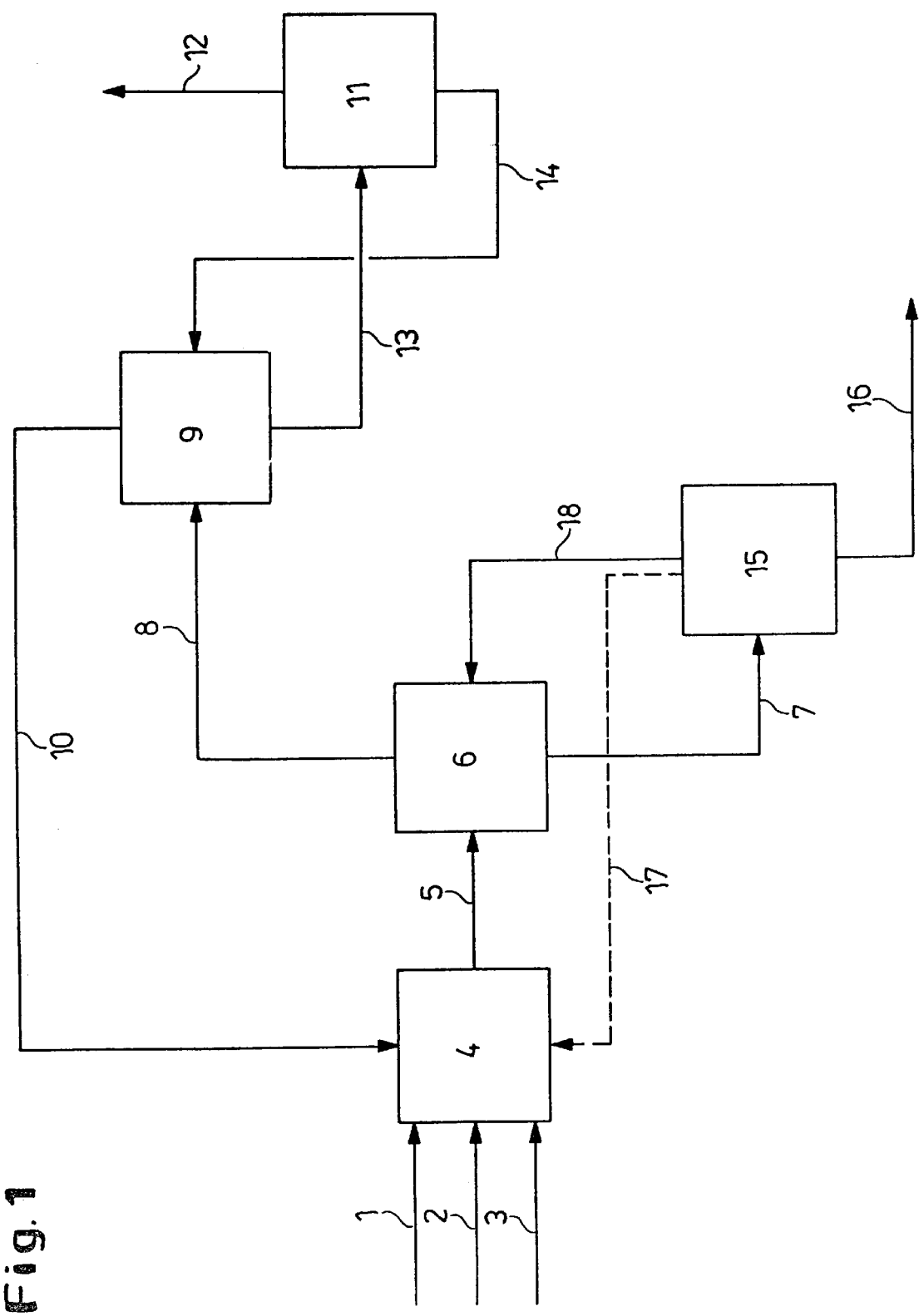
FIG. 1 shows a preferred embodiment of the process of the invention.

In the process of the invention, the formate salts formed are cleaved by distillation in the presence of an auxiliary into formic acid and the free nitrogen base, which can advantageously be returned to the process. Furthermore, the prior removal of the trimethylol compound from the product mixture ensures that no trimethylol formate esters are formed during the cleavage of the formate salts into formic acid and the free nitrogen base.

Formic acid is an important product that is used, for example, in the tanning of leather, for adjusting pH values, in dye manufacture, and for producing pharmaceutical products. In addition, formic acid is used in the coagulation of latex, as an additive for producing silage, and as promoter in fermentation processes.

The aldehydes used in the process of the invention are preferably those of the formula (I)

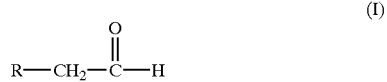

where

R represents methylol, straight-chain or branched $C_1$–$C_{12}$-alkyl, $C_3$–$C_8$-cycloalkyl, $C_6$–$C_{10}$-aryl or $C_7$–$C_{22}$-aralkyl, wherein each such radical is optionally further substituted with groups that are inert under the reaction conditions (e.g., alkyl groups or alkoxy groups having 1–3 carbon atoms).

If R represents a straight-chain or branched $C_1$–$C_{12}$-alkyl radical, R may be, for example, methyl, ethyl, propyl, isopropyl, n-butyl, sec-butyl, tert-butyl, pentyl, or hexyl. If R is a $C_3$–$C_8$-cycloalkyl radical, R may be, for example, cyclopropyl, cyclobutyl, cyclopentyl, cyclohexyl, cycloheptyl, or cyclooctyl. If R is a $C_6$–$C_{10}$-aryl radical, R may be, for example, phenyl or naphthyl. If R is a $C_7$–$C_{22}$-aralkyl radical, R may be, for example, benzyl.

In the process of the invention, the aldehydes of the formula (I) are, in particular, aldehydes in which R is methylol or straight-chain or branched $C_1$–$C_6$-alkyl. Particular preference is given to using aldehydes of the formula (I) in which R is methylol, methyl, ethyl, n-propyl, or isopropyl, very particularly preferably ethyl.

The formaldehyde used in the process of the invention can be used in gaseous form, in polymeric form, or in the form of an aqueous solution. If formaldehyde is used in polymeric form in the process of the invention, preference is given to using paraformaldehyde. Formaldehyde is preferably used in the process of the invention in the form of an aqueous solution, preferably a 1 to 55% strength by weight aqueous solution, more preferably a 5 to 35% strength by weight solution, particularly preferably a 10 to 32% strength by weight solution.

In the process of the invention, formaldehyde is preferably used in an excess over the aldehyde used. The molar ratio of aldehyde to formaldehyde is preferably 1:(3–10), particularly preferably 1:(3–5), very particularly preferably 1:(3–3.5).

Nitrogen bases that can be used in the process of the invention are those which are known as basic catalysts for aldol condensations and additionally make possible a Cannizzaro reaction between the aldehyde used and formaldehyde. Examples of such nitrogen bases are symmetrical trialkylamines such as trimethylamine, triethylamine, tri-n-propylamine, triisopropylamine, tri-n-butylamine, triisobutylamine, or tri-tert-butylamine; unsymmetrical trialkylamines such as ethyidimethylamine, isopropyl-dimethylamine, diethylmethylamine, dimethylpropylamine, isobutyl-dimethylamine, butyldimethylamine, tert-butyidimethylamine, dimethyl-pentylamine, (2,2-dimethylpropyl)dimethylamine, hexyldimethylamine, or dibutylheptylamine; diamines such as N,N,N',N'-tetramethylbutane-1,3-diamine, ethyldiisopropyldiamine, or N,N,N',N'-tetramethylethane-1,2-diamine; allylamines such as allyidimethylamine, allyldiethylamine, or triallylamine; aminoalcohols such as 4-dimethylaminoethanol, 2-dimethyl-aminobutanol, 2-diisopropylaminoethanol, diethylaminomethanol, diethyl-aminoethanol, 3-dimethylaminopropan-1-ol, or dimethylamino-2-methyl-propan-1-ol; alkoxy-substituted amines such as (2-methoxyethyl)dimethyl-amine, (3-methoxypropyl) dimethylamine, or diethylmethoxymethylamine; and hydroxylamines such as N,N-dimethylhydroxylamine.

Preference is given to using symmetrical tri-n-alkylamines such as trimethylamine, triethylamine, tri-n-propylamine, or tri-n-butylamine, particularly preferably trimethylamine and triethylamine.

Mixtures of various nitrogen bases can also be used in the process of the invention.

In the process of the invention, the nitrogen base is preferably used in an amount of from 1 to 10 mol, particularly preferably from 1 to 5 mol, very particularly preferably from 1 to 3 mol, per 1 mol of aldehyde.

In the first step of the process of the invention, an aldehyde, preferably an aldehyde of the formula (I), is reacted with formaldehyde, preferably with an aqueous formaldehyde solution, in the presence of a nitrogen base to form a trimethylol compound and the formate salt of the nitrogen base used.

The reaction preferably takes place at temperatures of from 10 to 150° C., particularly preferably from 30 to 130° C., very particularly preferably from 40 to 100° C.

The reaction can be carried out at atmospheric pressure, under subatmospheric pressure, or under superatmospheric pressure. If the reaction temperature chosen is above the boiling point of the components of the reaction mixture, the reaction can be carried out under super-atmospheric pressure. It is preferably carried out at atmospheric pressure.

The reaction can be carried out batchwise, semibatchwise, or continuously, preferably continuously. Possible reaction apparatuses are all reaction apparatuses that are known to those skilled in the art and are suitable for reacting liquid reactants. The reaction is preferably carried out in stirred tank reactors, cascades of stirred tanks, flow tubes, or multichamber reactors.

The residence time of the reaction mixture in the reactor can be, for example, from 10 minutes to 50 hours.

In a second step of the process of the invention, the trimethylol compound that is formed is removed from the product mixture. The trimethylol compound is preferably removed from the product mixture by extraction.

If the trimethylol compound is removed from the product mixture by extraction, it is possible to use alkanes, cycloalkanes, alcohols, ethers, aldehydes, ketones, or esters as extractants. Preference is given to using hexane, cyclohexane, isopropyl alcohol, isobutyl alcohol, 2-ethylhexanol, 2-ethyl-2-hexenol, cyclohexanol, tert-butyl methyl ether, butyraldehyde, propionaldehyde, methyl ethyl ketone, methyl isobutyl ketone, ethyl acetate, or butyl acetate. The extractant is particularly preferably the aldehyde that is reacted in the process of the invention to form the trimethylol compound. Very particular preference is given to using butyraldehyde as extractant.

The extraction can be carried out continuously or batchwise in any extraction apparatus known to those skilled in the art. The extraction is preferably carried out continuously, preferably in a mixer-settler apparatus, sieve tray column or packed column, pulsed sieve tray column or packed column, Karr column, Kühni column, or spray column or in a centrifugal extractor.

The mixture of extractant and trimethylol compound obtained in the extraction is preferably separated by distillation, particularly preferably by rectification.

After removal of the trimethylol compound, the remaining formate solution is, in the process of the invention, admixed with an auxiliary that has the task of binding the formic acid, as a result of which the nitrogen base is liberated.

The cleavage of formate salts of a nitrogen base into formic acid and the nitrogen base by use of bases is described, for example, in EP 181 078 A.

In the process of the invention, auxiliaries used are preferably substances that have a lower basicity than the nitrogen base used, that form adducts with formic acid that can be decomposed thermally at a temperature above the boiling point of the nitrogen base, and that have a low volatility. Auxiliaries are preferably compounds containing nitrogen and having a $pK_b$ of from 10 to 3.

Auxiliaries used in the process of the invention are preferably cyclic nitrogen compounds selected from the group consisting of imidazoles, quinolines, pyridines, pyrimidines, pyrroles, pyrazoles, isoquinolines, pyrazines, pyridazines, piperidines, pyrrolidines, and morpholines, each of which may bear one or more substituents selected from the group consisting of $C_1$–$C_6$-alkyl (preferably methyl, formyl or phenyl), for example, 2-, 3- and 4-methylpyridine, N-methylmorpholine, N-formylmorpholine, or N-phenylmorpholine. Preferred cyclic nitrogen compounds are N-formylmorpholine, dimorpholinoethane, quinoline, and imidazoles of the formula (II)

where
$R^1$ and $R^2$ each represent, independently of one another, hydrogen or straight-chain or branched $C_1$–$C_{24}$-alkyl (preferably straight-chain or branched $C_1$–$C_{10}$-alkyl such as methyl, ethyl, propyl, isopropyl, n-butyl, sec-butyl, tert-butyl, n-pentyl, n-hexyl, or n-heptyl).

In a further preferred embodiment, auxiliaries used are amides of the formula (III),

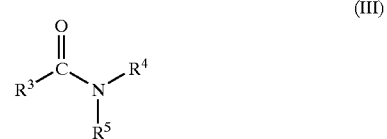

where
$R^3$ and $R^4$ each represent, independently of one another, straight-chain or branched $C_1$–$C_{24}$-alkyl (preferably straight-chain or branched $C_1$–$C_{10}$-alkyl such as methyl, ethyl, propyl, isopropyl, n-butyl, sec-butyl, tert-butyl, n-pentyl, n-hexyl, or n-heptyl), $C_6$–$C_{10}$-aryl such as phenyl or naphthyl, or $C_7$–$C_{22}$-aralkyl such as benzyl, and
$R^5$ represents hydrogen or is as defined for $R^3$ and $R^4$.

In a further preferred embodiment, auxiliaries used are cyclic amides of the formula (IV),

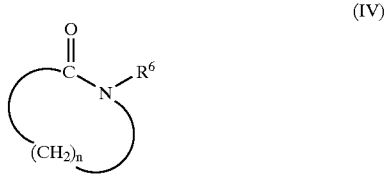

where
$R^6$ represents straight-chain or branched $C_1$–$C_{20}$-alkyl such as methyl, ethyl, propyl, isopropyl, n-butyl, sec-butyl, tert-butyl, n-pentyl, isopentyl, hexyl, isohexyl, nonyl, n-decyl, dodecyl, tridecyl, tetradecyl, hexadecyl, octadecyl, or 2-methylbutyl or a $C_2$–$C_{20}$-alkenyl radical such as vinyl, allyl, or buten-2-yl, and n represents a number from 3 to 6.

Auxiliaries used in the process of the invention are preferably cyclic amides of the formula (IV) in which n represents 3, particularly preferably cyclic amides of the formula (IV) in which n represents 3 and $R^6$ represents methyl or ethyl.

Further preferred auxiliaries are cyclic amides of the formula (IV) in which n represents 4, particularly preferably cyclic amides of the formula (IV) in which n represents 4 and $R^6$ represents methyl or ethyl.

Very particularly preferred compounds used as auxiliaries in the process of the invention are N-methylpyrrolidone, 1,2-dimorpholinoethane, N-formylmorpholine, N-methylacetamide, N,N-dimethylacetamide, N-ethylacetamide, N-butylimidazole, and N,N-diethylacetamide.

In the process of the invention, the auxiliaries are preferably used in an excess relative to the formic acid. Particular preference is given to using 1.1 to 5 mol of auxiliary per mol of formic acid.

After the cleavage of the formate salt of the nitrogen base formed in. the process of the invention into the free nitrogen base and formic acid by distillation in the presence of an auxiliary, the nitrogen base is preferably returned to the reaction process.

The distillation is preferably carried out at temperatures of from 10 to 300° C. (particularly preferably from 50 to 250° C.) and preferably at a pressure of from 1 mbar to 5 bar (particularly preferably from 1 mbar to 1 bar).

After the base, which is preferably returned to the reaction process, has been separated off by distillation, the formic acid is preferably separated thermally from the auxiliary. In a particularly preferred embodiment, this separation is achieved by extractive rectification since this enables a very pure formic acid to be obtained.

The separation of the formic acid from the auxiliary is preferably carried out at a temperature of from 100 to 300° C. and a pressure of from 1 to 200 mbar.

The bottoms comprising auxiliary and possibly small proportions of formic acid is preferably returned to the process.

FIG. 1 shows a preferred embodiment of the process of the invention. In this embodiment, the aldehyde used in the process of the invention is fed via stream 1 together with formaldehyde (stream 2) and nitrogen base, which comes mostly from the recycle stream 10 and to a lesser extent is added fresh via stream 3 to a reaction stage 4. In this reaction stage, the aldehyde is preferably reacted at temperatures of from 10 to 150° C. The resulting reaction mixture is passed as stream 5 to a separation stage 6 in which the trimethylol compound formed is removed from the product mixture, preferably by extraction. If desired, low boilers and/or part of the water can be removed beforehand from the product stream by distillation, a variant that is not shown in FIG. 1. The low boilers mentioned include, for example, incompletely reacted aldehyde, form-aldehyde, or nitrogen base, as well as by-products such as acroleins and in the case of the preparation of trimethylolpropane α-ethylacrolein. If low boilers are removed from the product stream by distillation, all or some of the distillate may, if desired, be returned to reaction stage 4.

If the trimethylol compound has been, in a preferred embodiment, removed from the product mixture by extraction, the extract is separated into the trimethylol compound (stream 16) and the extractant in a subsequent process stage 15, this separation preferably being carried out by rectification. The extractant used is preferably returned as stream 18 to the extraction stage 6 or, if the aldehyde employed in the process of the invention is used as extractant, wholly or partly returned as stream 17 to the reaction stage 4. If the aldehyde employed in the process of the invention is used as extractant, the fresh aldehyde fed in as stream 1 is, in a further preferred embodiment, firstly introduced into the extraction step 6.

The aqueous raffinate phase 8 that is obtained in the removal of the trimethylol compound from the product mixture and contains the formate salt is, according to the invention, converted into the free nitrogen base and formic acid by distillation in the presence of an auxiliary. For this purpose, the raffinate is preferably brought into contact with the auxiliary in a rectification column 9. The auxiliary is preferably fed as stream 14 into the upper part of the column. In a preferred embodiment, the aqueous raffinate phase 8 is fed into the middle part of a rectification column 9, so that the auxiliary stream 14 which is preferably fed into the upper part of the column is conveyed in countercurrent to the aqueous raffinate phase. In a preferred embodiment, the rectification column 9 is operated at pressures of 100 to 1,000 mbar. The distillate obtained in 9, which contains the nitrogen base used in the process and possibly residual water and low boilers, is preferably returned directly or after purification by distillation, a variant that is not shown in FIG. 1, as stream 10 to the reaction stage 4.

The bottom product from 9 consists essentially of the auxiliary used in the process of the invention and formic acid. The bottoms are preferably fed as stream 13 into a second rectification column 11, preferably in the middle region of the column. Rectification in the rectification column 11 separates the bottom product from 9 into the free formic acid as top product (stream 12) and auxiliary as bottom product (stream 14). The rectification can be carried out batchwise or continuously. The rectification is preferably carried out continuously. The rectification can be carried out in all rectification apparatuses known to those skilled in the art but preference is given to using columns provided with sieve trays, bubble cap trays, random packing, or ordered packing. The pure formic acid is usually obtained at a pressure of from 50 to 250 mbar and a temperature of from 20 to 60° C. The auxiliary obtained as bottom product is preferably returned to the distillation 9.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

PREPARATION OF TRIMETHYLOLPROPANE

Example 1

117.90 g of distilled water, 250.25 g (2.5 mol) of 30% strength aqueous formaldehyde solution, and 154.88 g (1.5 mol) of triethylamine were placed in a 1 liter glass reactor at 25° C. 36.46 g (0.5 mol) of butyr-aldehyde were subsequently metered in over a period of 45 minutes and the reactor temperature was at the same time increased linearly to 70° C. After the metered addition was complete, the mixture was stirred under reflux for another 3 hours. According to GC analysis, trimethylolpropane was obtained in a yield of 81.59% of theory.

Example 2

117.90 g of distilled water, 250.25 g (2.5 mol) of 30% strength aqueous formaldehyde solution, and 77.44 g (0.75 mol) of triethylamine were placed in a 1 liter glass reactor at 25° C. 36.46 g (0.5 mol) of butyr-aldehyde were subsequently metered in over a period of 45 minutes and the reactor temperature was at the same time increased linearly to 70° C. After the metered addition was complete, the mixture was stirred under reflux for another 3 hours. According to GC analysis, trimethylolpropane was obtained in a yield of 82.77% of theory.

Example 3

231.75 g of distilled water, 175.18 g (1.75 mol) of 30% strength aqueous formaldehyde solution, and 72.28 g (0.70 mol) of triethylamine were placed in a 1 liter glass reactor at 25° C. 36.46 g (0.5 mol) of butyr-aldehyde were subsequently metered in over a period of 45 minutes and the reactor temperature was at the same time increased linearly to 70° C. After the metered addition was complete, the mixture was stirred under reflux for another 4 hours. According to GC analysis, trimethylolpropane was obtained in a yield of 76.34% of theory.

EXTRACTION OF TRIMETHYLOLPROPANE

Example 4

100 g of an aqueous trimethylolpropane solution containing 10% by weight of trimethylolpropane and 15.4% by weight of triethylammonium formate were extracted three times in succession with 50 g of n-butyr-aldehyde. The combined organic phases (157.1 g) contained 7.7 g of TMP and 0.1 g of triethylammonium formate.

RECOVERY OF TRIETHYLAMINE

Example 5

A mixture of N-methylpyrrolidone (NMP), water and triethylammo-nium-formate was distilled in a distillation apparatus comprising a 1.6 m high silvered column filled with 4 mm mesh rings and a 1 liter still part. 623.8 g of a mixture consisting of 62.9% by weight of NMP, 22.3% by weight of triethylammonium formate, and 14.8% by weight of water were first placed in the apparatus and distilled at atmospheric pressure. At a reflux ratio of 10, 104.6 g of distillate were separated off at a temperature at the top of 76° C. The temperature at the bottom was 127–136° C. The distillate consisted of 88.3% by weight of triethylamine and 11.7% by weight of water. The recovery of triethylamine was thus 92%. Formic acid and NMP remained in the bottoms.

Example 6

560.7 g of a mixture consisting of 66.4% by weight of N-butylimid-azole, 20.8% by weight of triethylammonium formate, and 12.8% by weight of water were placed in the apparatus described in Example 5. At a reflux ratio of 10, 79.2 g of distillate were separated off at a temperature at the top of 76° C. The distillates contained 82.3% by weight of triethylamine and 17.7% by weight of water. The recovery rate of triethylamine was thus 85.8%. Formic acid and N-butylimidazole remained in the bottoms.

ISOLATION OF FORMIC ACID

Example 7

600 g a mixture of 16.7% by weight of formic acid and 83.3% by weight of NMP were placed in the apparatus described in Example 5. At 200 mbar and a reflux ratio of 10, 52.6 g of distillate were obtained at a temperature at the top of 56° C. The temperature at the bottom was 150–152° C.

The distillate contained 98.6% by weight of formic acid and 1.4% by weight of NMP.

What is claimed is:

1. A process for preparing trimethylol compounds and formic acid comprising
   (a) reacting formaldehyde and an aldehyde in the presence of a nitrogen base to form a product mixture containing the trimethylol compound and a formate salt of the nitrogen base,
   (b) removing the trimethylol compound from the product mixture after the reaction, and
   (c) cleaving the formate salts into the free nitrogen base and formic acid by distillation in the presence of an auxiliary.

2. A process according to claim 1 wherein the aldehyde has the formula (I),

where
   R represents methylol, straight-chain or branched $C_1$–$C_{12}$-alkyl, $C_3$–$C_8$-cycloalkyl, $C_6$–$C_{10}$-aryl, or $C_7$–$C_{22}$-aralkyl, wherein each such radical is optionally further substituted with groups that are inert under the reaction conditions.

3. A process according to claim 1 wherein the aldehyde is n-butyraldehyde.

4. A process according to claim 1 wherein the trimethylol compound is removed from the product mixture by extraction.

5. A process according to claim 4 wherein the extraction is carried out using an extractant selected from the group consisting of alkanes, cycloalkanes, alcohols, ethers, aldehydes, ketones, and esters.

6. A process according to claim 4 wherein the extraction is carried out using as the extractant the aldehyde that was reacted with formaldehyde according to claim 1 to form the trimethylol compound.

7. A process according to claim 1 wherein the auxiliary comprises compounds that have a lower basicity than the nitrogen base used and form adducts with formic acid that can be decomposed thermally at a temperature above the boiling point of the nitrogen base.

8. A process according to claim 1 wherein the auxiliary is a nitrogen-containing compound having a $pK_b$ of 10 to 3.

9. A process according to claim 1 wherein the auxiliary is
   (i) a cyclic nitrogen base selected from the group consisting of imidazoles, quinolines, pyridines, pyrimidines, pyrroles, pyrazoles, isoquinolines, pyrazines, pyridazines, piperidines, pyrrolidines, and morpholines,
   (ii) an amide of the formula (III),

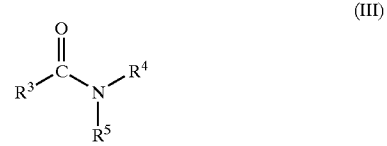

where
   $R^3$ and $R^4$ each represent, independently of one another, straight-chain or branched $C_1$–$C_{24}$-alkyl, $C_6$–$C_{10}$-aryl, or $C_7$–$C_{22}$-aralkyl, and
   $R^5$ represents hydrogen or is as defined for $R^3$ and $R^4$, or (iii) a cyclic amide of the formula (IV),

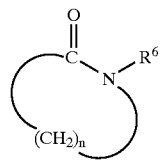

where
R[6] represents straight-chain or branched $C_1$-$C_{20}$-alkyl or a $C_2$-$C_{20}$-alkenyl radical, and
n represents a number from 3 to 6.

10. A process according to claim 1 wherein the auxiliary is N-methylpyrrolidone.

11. A process according to claim 1 wherein the distillation in the presence of an auxiliary is carried out in such a way that a stream containing the free nitrogen base is obtained as a top fraction and a stream containing the auxiliary and formic acid is obtained as a bottom fraction.

12. A process according to claim 11 wherein the bottom fraction is separated into the auxiliary and formic acid in a subsequent distillation and the separated auxiliary is returned to the distillation for cleavage of the formate salt.

* * * * *